(12) United States Patent
Noe'

(10) Patent No.: US 6,774,234 B1
(45) Date of Patent: Aug. 10, 2004

(54) MELAMINE PURIFICATION PROCESS

(75) Inventor: Sergio Noe', San Donato Milanese (IT)

(73) Assignee: Eurotecnica Group, S.A., Basel (CH)

( * ) Notice: Subject to any disclaimer, the term of this patent is extended or adjusted under 35 U.S.C. 154(b) by 0 days.

(21) Appl. No.: 10/130,517

(22) PCT Filed: Nov. 3, 2000

(86) PCT No.: PCT/IT00/00443

§ 371 (c)(1),
(2), (4) Date: Oct. 17, 2002

(87) PCT Pub. No.: WO01/36397

PCT Pub. Date: May 25, 2001

(30) Foreign Application Priority Data

Nov. 16, 1999 (IT) .......................................... MI99A2388

(51) Int. Cl.[7] .............................................. C07D 251/62
(52) U.S. Cl. ........................................ 544/203; 544/201
(58) Field of Search .................................. 544/201, 203

(56) References Cited

U.S. PATENT DOCUMENTS 3,161,638 A * 12/1964 Christoffel et al. ....... 260/249.7
3,637,686 A * 1/1972 Kokubo et al. .......... 260/249.7
4,408,046 A * 10/1983 Van Hardeveld ............ 544/201

FOREIGN PATENT DOCUMENTS

| EP | 091 174 | 10/1983 |
|---|---|---|
| WO | 95/06042 | 3/1995 |

* cited by examiner

Primary Examiner—Richard L. Raymond
Assistant Examiner—Venkataraman Balasubramanian
(74) Attorney, Agent, or Firm—Pauley Petersen & Erickson

(57) ABSTRACT

A process for the purification of melamine, deriving from urea, according to a high pressure non catalytic process, by means of polycondensates and other by-products transformation, which by-products derive from the melamine synthesis comprosing the following steps: dissolving in water the raw liquid melamine containing polycondensates and other melamine synthesis by-products, subjecting such solution to a treatment capable to remove dissolved $CO_2$ limiting its concentration to a value lower than 0.5 wt. %, submitting raw melamine solution, to the action of ammonia, in an amount of 5 to 25 wt. %, at a temperature of 100 to 250° C. and leaving the mixture to react for some minutes, recoving a solution having polycondensates concentration lower than 1000 ppm, typically less than 100 ppm.

14 Claims, No Drawings

MELAMINE PURIFICATION PROCESS

TECHNICAL FIELD

The present invention refers to a process for the purification of melamine manufactured by synthesis from urea, according to a high pressure, non-catalytic process, and more particularly a process which is able to transform certain impurities, resulting from melamine synthesis or subsequent manipulations, essentially into melamine.

BACKGROUND ART

It is well known that in the high pressure melamine synthesis from urea a series of by-products is formed which affects melamine purity.

Particularly in the reactor, during melamine synthesis, and subsequently in the containers wherein melted melamine resides at a temperature higher than 350° C., typical melamine deammoniating condensation products are formed in a large amount. This category of condensation products are hereinafter collectively referred to as polycondensates. The simplest product is melam resulting from two melamine molecule condensation and one ammonia molecule separation.

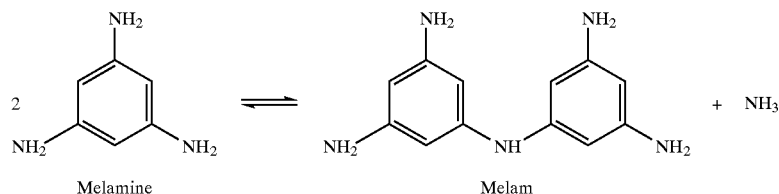

From two melamine molecules another product can be formed by separation of two ammonia molecules:

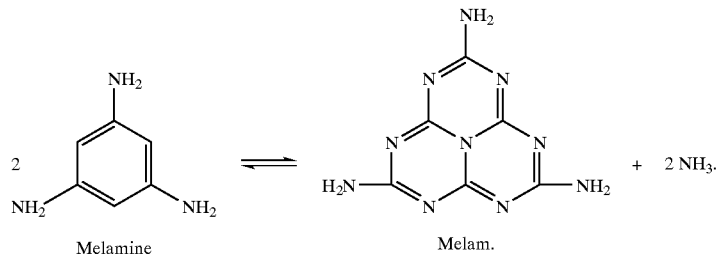

Another by-product resulting from melamine deammoniating condensation is melon:

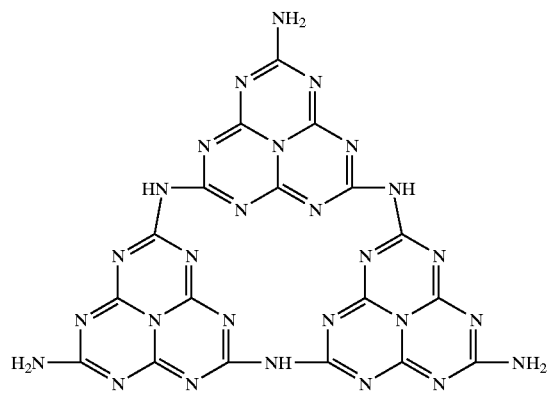

Generally liquid melamine (and therefore at a temperature higher than melting temperature of 350° C.), both inside reaction vessel and during the melamine residence in downstream treatment equipment, is subject to a chemical condensation associated with ammonia separation resulting in the formation of abovementioned products or even more complex ones collectively referred to as polycondensates. Polycondensates formation increases when ammonia partial pressure is lower and residence time of melted melamine is longer. These products are undesired for melamine use in the manufacture of formaldehyde/melamine condensation resins, therefore in the final melamine product a polycondensates content lower than 1000 ppm is requested as a minimum acceptable content.

Fortunately the reactions leading to these by-products are equilibrium reactions. Therefore melamine polluted by polycondensates may be purified, by subjecting said melamine to an ammonia action under suitable temperature and pressure conditions. Then, the ammonia action not only results in a polycondensates elimination, but due to the polycondensate transformation into melamine, an increase of global yield is also obtained.

However the operative conditions necessary to reach the above results are quite heavy and expensive in that they imply to subject melted melamine to an ammonia partial pressure higher than 250 bars ($2.5 \times 10^7$ Pa), preferably above 400 bars ($4 \times 10^7$ Pa), in order to obtain a melamine of an acceptable purity.

On the other hand the transformation of polycondensates to melamine in an aqueous medium requires less severe and less expensive operating conditions. In the industrial practice all melamine synthesis processes include a recovery and purification step of raw melamine coming out of the synthesis reactor in an aqueous medium.

Said process consists in sending the reaction product, comprising a raw melamine liquid phase and an essentially $NH_3$— and $CO_2$— containing gas phase, to an appropriate contacting equipment (quench tower) wherein the product is cooled down by means of water. Pressure is simultaneously reduced from reaction pressure (higher than 70 bars–$7 \times 10^6$ Pa) to a pressure of about 25 bars ($2.5 \times 10^6$ Pa) and at a temperature lower than 165° C. to limit both corrosion problems and the amount of steam entrained in vapour phase.

As a result of the above contact, a gas phase containing $NH_3$, $CO_2$ and steam and a liquid aqueous phase which contains melamine, polycondensates, unreacted urea as well as minor impurities are obtained. From the liquid phase, melamine is recovered, through several manipulation and crystallisation steps.

Typically, said solution has a melamine concentration of 5 to 15% w, and contains also some unreacted urea, dissolved gases as $NH_3$ and $CO_2$ as well as other minor impurities including the polycondensates. The latter are present in the amount of 1:30 to 1:70 with respect to dissolved melamine.

By subjecting this solution to ammonia action, the polycondensates transformation into melamine takes places; however, such reaction proceeds with a very low rate requiring a very long contact time to reach a polycondensates transformation degree matching the required purity specifications.

For this reason in the commercial plants, the liquid solution coming out of the quenching tower is kept as such, with or without any ammonia addition for a suitable period of time which may be of one to several hours. Said technique requires the use of large treatment volumes that means, taking into consideration the temperature and pressure conditions and the corrosive characteristics of the products under treatment, the use of special stainless steels, high apparatus thickness and, therefore, higher investment costs. Moreover in the course of the above treatment an undesirable loss of product takes place because of the contemporaneous melamine hydrolysis reaction in presence of water, which loss is higher, the longer is the treatment time necessary to reduce the polycondensates to an acceptable value.

There is not, at this moment, any available melamine purification process capable to reduce the impurity contents, particularly the by-products originated from the melamine deammoniating condensation, which do not require a melamine treatment under severe temperature and pressure conditions or capable to reduce the reaction time to an economically acceptable value. The present invention intends to solve the abovementioned problems.

DISCLOSURE OF THE INVENTION

It has been surprisingly found that the conversion rate of polycondensates to melamine in an aqueous environment in presence of ammonia, which, as we saw, is very low, may considerably increase if the $CO_2$ content of the aqueous solution deriving from the water quenching of the reaction products is reduced to a value lower than 0.5 and preferably lower than 0.2% wt.

DETAILED DESCRIPTION OF THE INVENTION

It is therefore a first object of the present invention a process for the purification of melamine, deriving from urea, according to a high pressure non-catalytic process, by means of polycondensates and other by-products transformation, which by-products derive from the melamine synthesis, comprising the following steps:

a) dissolving in water the raw liquid melamine coming out of the synthesis reactor and containing polycondensates and other melamine synthesis by-products;

b) subjecting such solution to a treatment capable to remove the dissolved $CO_2$, limiting its concentration to a value lower than 0.5% wt, preferably lower than 0.2% wt;

c) reacting the obtained solution with ammonia in an amount in a range of 5 to 25%, preferably 12 to 15% by weight at a temperature in the range of 130 to 250° C., preferably 160 to 180° C., and keeping the mixture to react for some minutes;

d) collecting the solution having a polycondensates concentration lower than 1000 ppm, typically lower than 100 ppm.

The $CO_2$ content reduction, in the second step b), may preferably be obtained by stripping the solution with a gas that is inert with respect of the solution components. Preferably the solution stripping gas is steam, which does not leave any extraneous component.

As a matter of fact by submitting raw melamine solution, coming out of quenching tower, to a steam stripping action, ammonia and $CO_2$ are almost completely removed. The operation is carried out in such a way as to reduce as much as possible any residual $CO_2$ concentration in the melamine solution and, in any case, to a $CO_2$ concentration lower than 0.5% by weight, preferably lower than 0.2% based on the total weight of the melamine solution.

By submitting raw melamine solution, coming out of quenching tower, to ammonia action, in an amount of 5 to 25% wt preferably 12 to 15% wt, at a temperature of 130 to 250° C., preferably 160 to 180° C. and under the resulting equilibrium pressure, polycondensates originally present in the solution completely disappear in a few minutes of reaction and are not detected when analysed with ultraviolet spectrophotometer in the melamine final product (analytical limit<10 ppm).

From the abovesaid it results that is very convenient to submit the solution of raw melamine to the action of ammonia when $CO_2$ is practically absent or the relevant amount is very low (less than 0.5% wt or preferably less than 0.2% wt).

BEST MODE TO CARRY OUT THE INVENTION

The following examples show the extent of the advantages deriving from the practice of this invention, but are not to be interpreted as restricting the scope of the invention.

EXAMPLE 1

Melamine non-catalytic synthesis from urea, according to the high pressure process is carried out in an internal circulation reaction vessel operating at 390° C. and $8.0 \times 10^6$ Pa (80 bars).

The reaction product coming out of the reactor consists of a liquid phase and a gas phase having the following compositions (by weight):

| Gas phase (about 65% of total products coming out of the reactor): | |
| --- | --- |
| $NH_3$ | 46.5% |
| $CO_2$ | 50% |
| Melamine (vapour) | 3.5% |
| Liquid phase (about 35% of total products coming out of the reactor): | |
| Melamine | 88% |
| OAT (oxyaminotriazines) | 2.7% |
| Polycondensates | 2.2% |
| Dissolved $NH_3$ | 1.3% |
| Dissolved $CO_2$ | 0.8% |
| Unreacted urea | 5% |

Both liquid and gas phases are contacted with water in the quenching tower under $2.5 \times 10^6$ Pa gauge (25 bars gauge) and at 162° C.

From quenching tower a gas phase containing water, $NH_3$, and $CO_2$ is collected with the following composition (by weight):

| | |
|---|---|
| $H_2O$ | 20% |
| $CO_2$ | 38% |
| $NH_3$ | 42% |

And a solution phase which contains all melamine having the following composition by weight:

| | |
|---|---|
| $H_2O$ | 68.5% |
| Melamine | 10% |
| OAT | 0.3% |
| Polycondensates | 0.23% |
| Urea | 0.47% |
| $NH_3$ | 16.7% |
| $CO_2$ | 3.8% |

The above solution is subject to stripping with steam under the following conditions: 5 bars ($5 \times 10^5$ Pa gauge) and 160° C. at bottom column. The solution recovered from the bottom of the column has the following composition (by weight):

| | |
|---|---|
| $H_2O$ | 88.7% |
| Melamine | 9.5% |
| OAT | 0.32% |
| Polycondensate | 0.24% |
| Urea | 0.4% |
| $NH_3$ | 0.51% |
| $CO_2$ | 0.33% |

The above water solution is added with ammonia up to a concentration higher than 13% by weight and then is left to react in a suitable column under $2.5 \times 10^6$ Pa gauge (25 bars) and 172° C. Residence time of the above solution added with ammonia was about 15 minutes and the polycondensates concentration at the column outlet was lower than the minimum detectable amount by the selected analytical method.

Since the minimum detectable value of the analytical method, based on the Ultraviolet spectrophotometric technique, is 10 ppm with respect to the amount of melamine, it derives that with the inventive method a melamine solution is obtained, practically free from polycondensates.

EXAMPLE 2 (COMPARATIVE)

Same ammonia treatment was made on the raw melamine solution of Example 1 before the steam stripping operation (i.e. in presence of $CO_2$ in an amount corresponding to the conditions of quenching tower). Residual polycondensates concentration in the melamine product was clearly analytically detected and its concentration was always over 2000 ppm with respect to melamine, even after some hours of ammonia treatment at the conditions specified in the preceding example.

What is claimed is:

1. A process for the purification of melamine, derived from urea according to a high pressure non-catalytic process, by a reduction of a melamine polycondensate content to a concentration of lower than 100 ppm, comprising the following steps:

dissolving in water, raw liquid melamine coming out of a synthesis reactor and containing polycondensates and other melamine synthesis by-products thereby creating a solution;

subjecting the solution to a treatment capable of removing dissolved $CO_2$, reducing a concentration of the dissolved $CO_2$ to a value lower than 0.35% wt. thereby creating a raw melamine solution;

adding the raw melamine solution to ammonia, in an amount of 5 to 25% wt, at a temperature of 160 to 180° C. and leaving a resulting mixture to react; and recovering a purified solution from the resulting mixture, the purified solution having polycondensates concentration lower than 100 ppm.

2. A process for the purification of melamine, derived from urea, by a reduction of the melamine polycondensate content to a concentration of lower than 100 ppm according to claim 1, characterized in that $CO_2$ concentration in the solution is reduced to a value lower than 0.2% wt.

3. A process for the purification of melamine, derived from urea, by a reduction of the melamine polycondensate content to a concentration of lower than 100 ppm according to claim 2, characterized in that the ammonia utilized in the solution treatment is comprised from 12 to 15%.

4. A process for the purification of melamine, derived from urea, by a reduction of the melamine polycondensate content to a concentration of lower than 100 ppm according to claim 3, characterized in that the raw melamine solution is obtained by water quenching of the reaction mixture.

5. A process for the purification of melamine, derived from urea, by a reduction of the melamine polycondensate content to a concentration of lower than 100 ppm according to claim 1, characterized in that the reduction of $CO_2$ is obtained by solution stripping with an inert gas, preferably steam.

6. A process for the purification of melamine, derived from urea, by a reduction of the melamine polycondensate content to a concentration of lower than 100 ppm according to claim 1, characterized in that the raw melamine solution is obtained by water quenching the reaction mixture.

7. A process for the purification of melamine, derived from urea, by a reduction of the melamine polycondensate content to a concentration of lower than 100 ppm according to claim 2, characterized in that the raw melamine solution is obtained by water quenching of the reaction mixture.

8. A process for the purification of melamine, derived from urea, by a reduction of the melamine polycondensate content to a concentration of lower than 100 ppm according to claim 4, characterized in that the reduction of $CO_2$ is obtained by solution stripping with an inert gas, preferably steam.

9. A process for the purification of melamine, derived from urea according to a high pressure non-catalytic process, by a reduction of a melamine polycondensate content to a concentration of lower than 100 ppm, comprising the following steps:

dissolving in water, raw liquid melamine coming out of a synthesis reactor and containing polycondensates and other melamine synthesis by-products thereby creating a solution;

subjecting the solution to a treatment capable of removing dissolved $CO_2$, reducing concentration of the dissolved $CO_2$ to a value lower than 0.35% wt. thereby creating a raw melamine solution;

adding the raw melamine solution to ammonia, in an amount of 12 to 15% wt, at a temperature of 160 to 180° C. and leaving a resulting mixture to react; and recovering a purified solution from the resulting mixture, the purified solution having polycondensates concentration lower than 100 ppm.

10. A process for the purification of melamine, derived from urea according to a high pressure non-catalytic process, by a reduction of a melamine polycondensate content to a concentration of lower than 100 ppm, comprising the following steps:

a) dissolving in water, the raw liquid melamine coming out of a synthesis reactor and containing polycondensates and other melamine synthesis by-products to create a solution;

b) stripping the solution with an inert gas;

c) adding ammonia to the solution, in an amount of 5 to 25% wt., at a temperature of 160 to 180° C. and allowing a resulting mixture to react; and d) recovering a purified solution from the resulting mixture, the purified solution having a polycondensates concentration lower than 100 ppm.

11. A process for the purification of melamine, derived from urea, by a reduction of the melamine polycondensate content to a concentration of lower than 100 ppm according to claim 10, characterized in that a $CO_2$ concentration in the solution is reduced to a value lower than 0.2% wt.

12. A process for the purification of melamine, derived from urea, by a reduction of the melamine polycondensate content to a concentration of lower than 100 ppm according to claim 10, characterized in that an amount of ammonia utilized in the solution is comprised from 12 to 15%.

13. A process for the purification of melamine, derived from urea, by a reduction of the melamine polycondensate content to a concentration of lower than 100 ppm according to claim 1, characterized in that the purified solution is obtained by water quenching the resulting mixture.

14. A process for the purification of melamine, derived from urea, by a reduction of the melamine polycondensate content to a concentration of lower than 100 ppm according to claim 1, characterized in that a reduction of $CO_2$ is obtained by stripping the solution with steam.

* * * * *